United States Patent [19]

Karino et al.

[11] Patent Number: 5,811,571
[45] Date of Patent: Sep. 22, 1998

[54] PROCESS FOR PREPARING AROMATIC OR HETEROAROMATIC SULFONYL HALIDES

[76] Inventors: Hitoshi Karino; Hiroshi Goda; Jun-ichi Sakamoto; Katsuhiko Yoshida; Hideaki Nishiguchi, all of c/o Research Laboratory-1 Sumitomo Seika Chemicals Co., Ltd., 346-1 Miyanishi Harima-cho, Kako-gun Hyogo 675-01, Japan

[21] Appl. No.: 765,246
[22] PCT Filed: Dec. 25, 1995
[86] PCT No.: PCT/JP95/02675
    § 371 Date: Dec. 13, 1996
    § 102(e) Date: Dec. 13, 1996
[87] PCT Pub. No.: WO96/33167
    PCT Pub. Date: Oct. 24, 1996

[30] Foreign Application Priority Data

Apr. 17, 1995 [JP] Japan ................... 7-090993

[51] Int. Cl.$^6$ .................................................. C07C 255/10
[52] U.S. Cl. ............................................................ 558/413
[58] Field of Search ............................................ 558/413

[56] References Cited

FOREIGN PATENT DOCUMENTS

0094821A1  5/1983  European Pat. Off. .

OTHER PUBLICATIONS

Oxidative Chlorination of —Halogenosulphides as a Synthetic Route to —Halogenosulphoxides, Sulphinyl Chlorides, and Sulphonyl Chlorides by J.S. Grossert, et al. J. Chem. Soc., Chem. Commun. 1973, No. 2, p.50.

*Primary Examiner*—Deborah C. Lambkin
*Assistant Examiner*—Ebenezer O. Sackey
*Attorney, Agent, or Firm*—Knobbe, Martens, Olson & Bear, LLP

[57] ABSTRACT

The present invention is directed to a process for preparing an aromatic or heteroaromatic sulfonyl halide represented by the formula (3), the process comprising halogenating an aromatic or heteroaromatic methyl sulfide represented by the formula (1) or an aromatic or heteroaromatic methyl sulfoxide represented by the formula (2) with a halogenating agent in the presence of water $$Ar\text{-}(SCH_{3-m}X_m)_n \quad (1)$$

$$Ar\text{-}(SOCH_{3-m}X_m)_n \quad (2)$$

$$Ar\text{-}(SO_2Y)_n \quad (3)$$

wherein Ar is an aromatic ring or a heteroaromatic ring which is unsubstituted or which has an optional substituent or substituents, X and Y are halogen atoms, m is an integer of 0 to 3 and n is 1 or 2. According to the present invention, aromatic or heteroaromatic sulfonyl halides can be produced industrially cheaply and easily.

15 Claims, No Drawings

PROCESS FOR PREPARING AROMATIC OR HETEROAROMATIC SULFONYL HALIDES

FIELD OF THE INVENTION

This application is a 371 of PCT/JP 95/02675 filed on Dec. 12, 1995.

The present invention relates to a novel process for preparing aromatic or heteroaromatic sulfonyl halides. Aromatic or heteroaromatic sulfonyl halides are useful compounds which are used in various applications as pharmaceuticals, agricultural chemicals, functional materials or the like.

BACKGROUND ART

Many processes have been known for preparing aromatic sulfonyl halides. These processes are classified as follows.

(A) Process involving sulfonation

Halogen substitution reaction of sulfonate R. Adams, C. S. Marvel, Org. Synth., I,84 (1941)

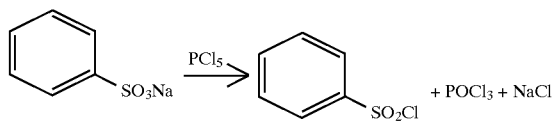

Sulfonation with chlorosulfuric acid or the like M. S. Morgan, L. H. Cretcher, J. Am. Chem. Soc., 70.375 (1948)

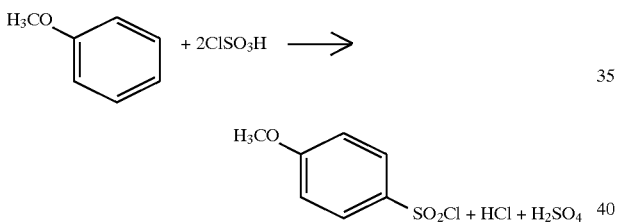

(B) Process involving formation of diazonium salt
H. Meerwein, E. Buchner, K. van Emster, J. Prakt, Chem., [2]152.251 (1939)

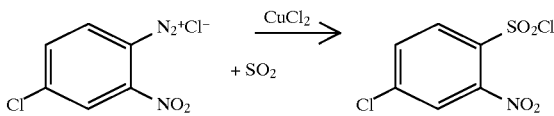

(C) Process utilizing metallization reaction
T. Hamada and O. Yonemitsu, Synthesis, 1986, 852

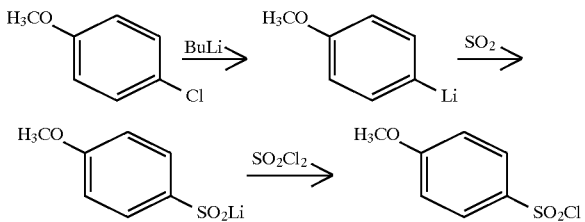

(D) Process involving chlorination of thiol derivative
I. B. Douglass, T. B. Johnson, J. Am. Chem. Soc., 60, 1486 (1938)

Y. J. Park, H. Hyun, Y. H. Kim, Chem. Lett., 1483, 1992

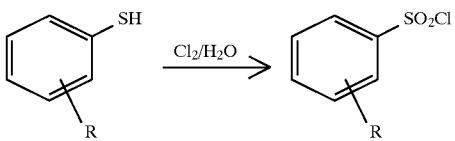

However, these known processes entail the following drawbacks when industrially carried out.

In the process (A), it is difficult to conduct a reaction in case of an aromatic ring having a nitro group, a cyano group, a carboxyl group or the like attached thereto or in case of a pyridine ring. In this process, generally at least two halogenated sulfonyl groups can not be easily introduced into one aromatic ring.

The process (B) tends to involve a lengthy procedure and poses a problem about the disposal of waste water which arises from the use of a large amount of copper salt. Thus the process is undesirable from the viewpoints of economy and protection of environment. Further, a diazonium salt itself is far from being stable and problematic as to safe operation.

The process (C) if industrially practiced does not economically pay in many instances because of a low yield and an expensive reagent used.

In the process (D), an aromatic substituted thiol derivative to be used as the raw material is often difficult to obtain at low costs on an industrial scale.

As described above, conventional processes for preparing aromatic sulfonyl halides are uneconomical and are not easy to industrially carry out in most cases. Consequently there has been a demand for processes capable of industrially manufacturing various aromatic sulfonyl halide derivatives at low costs.

DISCLOSURE OF THE INVENTION

It is an object of the present invention to provide a process for preparing an aromatic or heteroaromatic sulfonyl halide industrially at low costs and with ease.

The present inventors conducted extensive research to overcome the foregoing prior art drawbacks and to provide a process for preparing an aromatic or heteroaromatic sulfonyl halide industrially at low costs and with ease.

The finding was that the contemplated aromatic or heteroaromatic sulfonyl halides can be produced in high yields when using an aromatic or heteroaromatic sulfide or an aromatic or heteroaromatic sulfoxide as the raw material and halogenating said compound in the presence of water. The present invention was completed based on this novel finding.

While the reaction mechanism remains to be clarified, it is presumed that a bond between the sulfur atom and the carbon atom of methyl group in the aromatic or heteroaromatic methyl sulfide or the aromatic or heteroaromatic methyl sulfoxide used as the raw material is selectively and easily split, and the oxidation or halogenation of the sulfur atom occurs substantially coincidentally.

The first invention of the present application provides a novel process for preparing an aromatic or heteroaromatic sulfonyl halide represented by the formula (3), the process comprising halogenating an aromatic or heteroaromatic methyl sulfide represented by the formula (1) shown below with a halogenating agent in the presence of water

wherein Ar is an aromatic ring or a heteroaromatic ring which is unsubstituted or which has an optional substituent or substituents, X and Y are halogen atoms, m is an integer of 0 to 3 and n is 1 or 2.

The second invention of the present application provides a novel process for preparing an aromatic or heteroaromatic sulfonyl halide represented by the formula (3), the process comprising halogenating an aromatic or heteroaromatic methyl sulfoxide represented by the formula (2) shown below with a halogenating agent in the presence of water

(2)

(3)

wherein Ar is an aromatic ring or a heteroaromatic ring which is unsubstituted or which has an optional substituent or substituents, X and Y are halogen atoms, m is an integer of 0 to 3 and n is 1 or 2.

According to the present invention, a halogenated sulfonyl group can be easily introduced into an aromatic ring having a cyano group or the like as a substituent or a pyridine ring, and one or two halogenated sulfonyl groups can be easily introduced into one aromatic ring, although heretofore the synthesis has been difficult or a multi-step procedure has been necessitated.

The present invention is specifically described below in detail.

The sulfide and sulfoxide represented by the formulas (1) and (2), respectively which are used as the raw materials in the present invention include those prepared by any methods and can be more easily prepared, e.g. by the process for preparing 2,5-dichloroalkylthio-benzene which process was elucidated by the present inventors (Japanese Unexamined Patent Publication (Kokai) No.56760/1994).

Stated more specifically, the sulfide useful as the raw material can be easily prepared by reacting an aromatic or heteroaromatic compound having no substituent or having an optional substituent or substituents with an alkanethiol in a heterogeneous system, that is, in the presence of a base and a quaternary ammonium salt as a catalyst in water or a water/water-insoluble organic solvent mixture. A sulfoxide or a halomethyl sulfide can be produced by the oxidation or halogenation of the obtained sulfide.

The aromatic or heteroaromatic rings represented by Ar in the formulas are not specifically limited in the present invention and include a wide variety of aromatic or heteroaromatic rings which are unsubstituted or which have an optional substituent or substituents. Examples of useful aromatic or heteroaromatic rings are a benzene ring, naphthalene ring, pyridine ring, pyrazole ring, pyrazine ring, triazine ring, triazole ring, oxazole ring, isoxazole ring, thiazole ring, isothiazole ring, thiophene ring, benzothiophene ring, furan ring, benzofuran ring, pyrrole ring, indole ring, etc. Preferred examples are a benzene ring, pyridine ring, thiophene ring, thiazole ring and isothiazole ring.

Examples of optional substituents are halogen, cyano group, nitro group, formyl group, alkylcarbonyl group, carboxyl ester group, carbamoyl group, alkyl group, alkoxyl group, substituted phenylthio group, etc.

X in the sulfide of the formula (1) or in the sulfoxide of the formula (2) represents a chlorine atom or a bromine atom. Economically the compound wherein X is a chlorine atom is preferred. While m is an integer of 0 to 3, a compound wherein m is 0 is generally easily available. However, when the yield of the desired product is to be increased, a better result is given by a compound wherein m is 1, namely a halomethyl sulfide or a halomethyl sulfoxide, or a compound wherein m is 2, namely a dihalomethyl sulfide or a dihalomethyl sulfoxide.

In the present invention, the reaction is made to proceed for converting a sulfide or a sulfoxide to a sulfonyl halide in a high yield by the addition of a halogenating agent in the presence of water. The amount of water to be used in the present invention is not specifically determinable since it is variable depending on the sulfide or sulfoxide selected as the raw material. Yet, usually the amount of water to be used is 1 to 100 moles, preferably 3 to 50 moles, per mole of the sulfide or sulfoxide used as the raw material.

The halogenating agent used in the reaction includes, for example, chlorine, bromine, sulfuryl chloride, sulfuryl bromide and so on among which chlorine is preferred from the economical viewpoint. The amount of the halogenating agent to be used is not specifically determinable because it is variable depending on the raw material used. Yet, usually the amount is 2 to 50 moles, preferably 3 to 20 moles, per mole of the sulfide or sulfoxide used as the raw material.

There is no specific limitation on the solvent insofar as it is inert to the sulfonyl halides produced. While water can be used, useful solvents are various and include hydrocarbons such as hexane, cyclohexane and heptane, halogenated hydrocarbons such as dichloroethane, dichloromethane and chloroform, and aromatic hydrocarbons such as chlorobenzene, dichlorobenzene and trichlorobenzene. When a solvent is used, the amount of the solvent is not specifically limited but is usually 0.1 to 10 times the weight of the sulfide or sulfoxide.

The reaction temperature is usually in the range of −10° to 100° C., preferably 0° to 50° C. If the reaction temperature is too low, the reaction rate is reduced, whereas if the reaction temperature is too high, a side reaction occurs, leading to a low yield. The reaction time is usually in the range of about 0.5 to about 10 hours.

The aromatic or heteroaromatic sulfonyl halide thus obtained can be easily isolated by common distillation or crystallization.

The aromatic or heteroaromatic sulfonyl halides which can be produced according to the present invention include various compounds such as 4-chlorobenzenesulfonyl chloride, 4-bromobenzenesulfonyl bromide, 2,5-dichlorobenzenesulfonyl chloride, 1,2-benzenedisulfonyl chloride, 4-nitrobenzenesulfonyl chloride, 2-nitrobenzenesulfonyl chloride, 4-cyanobenzenesulfonyl chloride, 2-cyanobenzenesulfonyl chloride, 4-methylbenzenesulfonyl chloride, (4-chlorosulfonylphenyl)ethyl ketone, 4-chlorosulfonylbenzoic acid amide, 4-chlorosulfonylbenzoic acid methyl ester, 2-cyano-3-chlorobenzenesulfonyl chloride, (4-chlorosulfonyl-phenyl) phenyl sulfide, 2-chlorosulfonylpyridine, 2,6-dichlorosulfonylpyridine, 2-chlorosulfonylthiophene, 2,5-dichlorosulfonylthiophene, 2-chlorosulfonylpyrazine, 4-chlorosulfonyltriazole, 2-chlorosulfonyloxazole, 4-chlorosulfonylisoxazole, 2-chlorosulfonylthiazole, 4-chlorosulfonylisothiazole and so on. Preferred are 2-cyanobenzenesulfonyl chloride, 4-cyanobenzenesulfonyl chloride, 2-nitrobenzenesulfonyl chloride and 4-nitrobenzenesulfonyl chloride.

The compounds which can be produced in the present invention are not limited at all to the examples given above.

The present invention provides a novel process for preparing aromatic or heteroaromatic sulfonyl halides which are used in various applications as pharmaceuticals, agricultural chemicals, functional materials and so on. According to the process of the present invention, the contemplated product can be obtained in a high yield by a simple process comprising halogenating an industrially available aromatic or heteroaromatic methyl sulfide or aromatic or heteroaromatic methyl sulfoxide in the presence of water. Thus, the process of the invention is of economically, industrially high value.

BEST MODE FOR CARRYING OUT THE INVENTION

The present invention is described below in more detail with reference to the following examples to which, however, the invention is not limited in any way.

EXAMPLE 1

4-cyanophenyl methyl sulfide used as the raw material was prepared in accordance with the process disclosed in Japanese Unexamined Patent Publication (Kokai) No. 56760/1994. Stated more specifically, 165.1 g (1.2 moles) of 1-chloro-4-cyanobenzene and 17.8 g (0.055 mole) of tetra-n-butylammonium bromide as a phase transfer catalyst were added to a 2-liter, 4-necked flask equipped with a stirrer, thermometer and condenser. Then, 616.0 g (1.3 moles) of an aqueous solution of a sodium salt of methanethiol adjusted to a concentration of 15% by weight was added. The mixture was stirred at 80° C. for 3 hours. The reaction mixture was cooled to room temperature, and the precipitated crystals were collected by filtration and recrystallized from methanol, giving 170.4 g of 4-cyanophenyl methyl sulfide.

The 4-cyanophenyl methyl sulfide thus obtained (149.0 g, 1.00 mole) was charged into a 2-liter, 4-necked flask equipped with a stirrer, thermometer, condenser and gas inlet tube. To the flask was added 80 g of water and 800 g of monochlorobenzene after which 497 g (7.00 moles) of chlorine was blown into the flask at 25° C. over a period of about 5 hours to complete the reaction. After completion of the reaction, the oil layer was separated, about 50 g of anhydrous sodium sulfate was added and the mixture was left to stand for about 1 hour to remove the water. Thereafter the solvent was distilled off to give crude crystals. The crude crystals were dissolved in monochlorobenzene. A poor solvent was added for recrystallization to produce 183.5 g of 4-cyanobenzene-sulfonyl chloride as white crystals in a yield of 91% as calculated based on 4-cyanophenyl methyl sulfide.

EXAMPLES 2 TO 26

The same procedure as described in the latter part of Example 1 was conducted with the exception of altering the aromatic or heteroaromatic methyl sulfide used as the starting material to the compounds as shown below in Tables 1, 2 and 3, giving the corresponding aromatic or heteroaromatic sulfonyl chlorides.

TABLE 1

| Ex. | Starting Material | Product | Yield (%) |
| --- | --- | --- | --- |
| 2 | 4-Chlorophenyl methyl sulfide | 4-Chlorobenzenesulfonyl chloride | 90.2 |
| 3 | 2-Chlorophenyl trichloromethyl sulfide | 2-Chlorobenzenesulfonyl chloride | 92.1 |
| 4 | 2-Chlorophenyl methyl sulfoxide | 2-Chlorobenzenesulfonyl chloride | 90.2 |
| 5 | 2,4-Dichlorophenyl methyl sulfide | 2,4-Dichlorobenzene sulfonyl chloride | 94.1 |
| 6 | 2,5-Dichlorophenyl dichloromethyl sulfide | 2,5-Dichlorobenzenesulfonyl chloride | 92.5 |
| 7 | 2,6-Dibromophenyl chloromethyl sulfide | 2,6-Dibromobenzenesulfonyl chloride | 94.5 |
| 8 | 3,5-Dibromophenyl methyl sulfoxide | 3,5-Dibromobenzenesulfonyl chloride | 93.0 |
| 9 | 4-Bromophenyl chloromethyl sulfide | 4-Bromobenzenesulfonyl chloride | 89.0 |
| 10 | 4-Bromophenyl dichloromethyl sulfide | 4-Bromobenzenesulfonyl chloride | 91.2 |
| 11 | 1,4-Di(dichloromethylthio)benzene | 1,4-Benzenedisulfonyl chloride | 85.2 |

TABLE 2

| Ex. | Starting Material | Product | Yield (%) |
| --- | --- | --- | --- |
| 12 | 1,4-Di(methylsulfinyl)benzene | 1,4-Benzenedisulfonyl chloride | 86.4 |
| 13 | 1,2-Dimethylthiobenzene | 1,2-Benzenedisulfonyl chloride | 82.3 |
| 14 | 1,2-Dimethylthio-4-butylbenzene | 4-Butyl-1,2-benzenedisulfonyl chloride | 82.6 |
| 15 | 4-Cyanophenyl chloromethyl sulfide | 4-Cyanobenzenesulfonyl chloride | 95.0 |
| 16 | 2-Cyanophenyl dichloromethyl sulfide | 2-Cyanobenzenesulfonyl chloride | 85.0 |
| 17 | 4-Nitrophenyl chloromethyl sulfoxide | 4-Nitrobenzenesulfonyl chloride | 95.0 |
| 18 | 2-Nitrophenyl methyl sulfide | 2-Nitrobenzenesulfonyl chloride | 95.0 |
| *19 | Methyl 4-(methylthio)benzoate | Methyl 4-(chlorosulfonyl)benzoate | 90.1 |
| 20 | 2-Cyano-3-chlorophenyl methyl sulfide | 2-Cyano-3-chlorobenzenesulfonyl chloride | 93.1 |

TABLE 3

| Ex. | Starting Material | Product | Yield (%) |
|---|---|---|---|
| 21 | 4,4'-Di(methylthio)diphenyl sulfide | 4,4'-Di(chlorosulfonyl)diphenyl sulfide | 94.5 |
| 22 | 4,4'-Di(methylthio)-2,2'-(dicyano)diphenyl sulfide | 2,2'-(Dicyano)-4,4'-di(chlorosulfonyl)diphenyl sulfide | 95.6 |
| 23 | 4-(Phenylsulfonyl)phenyl methyl sulfide | 4-(Phenylsulfonyl)phenylsulfonyl chloride | 92.1 |
| 24 | 1-Naphthyl methyl sulfide | 1-Naphthylsulfonyl chloride | 92.8 |
| 25 | 1-Cyano-4-methyithio-naphthalene | 1-Cyano-4-chlorosulfonyl-naphthalene | 92.8 |
| 26 | Methyl 3-methylthio-2,5-thiophene-dicarboxylate | Methyl 3-chlorosulfonyl-2,5-thiophenedicarboxylate | 85.2 |

EXAMPLE 27

A 2-liter, 4-necked flask equipped with a stirrer, thermometer, condenser and a dropping funnel having a by-pass was charged with 20.4 g (0.10 mole) of 4-nitrophenyl methyl sulfide, 10 g of water and 200 g of monochlorobenzene. Then, 94.5 g (0.70 mole) of sulfuryl chloride was added dropwise at 10° C. over a period of about 2 hours. Thereafter the mixture was stirred at 10° C. for 6 hours to complete the reaction. After completion of the reaction, the oil layer was separated and 10 g of water was added to accomplish washing. Then, the oil layer was separated and left to stand for about 1 hour with the addition of about 5 g of anhydrous sodium sulfate to remove the water. The solvent was distilled off to give crude crystals. The crude crystals were dissolved in monochlorobenzene and a poor solvent was added for recrystallization, giving 21.1 g of 4-nitrobenzenesulfonyl chloride as white crystals in a yield of 95% as calculated based on 4-nitrophenyl methyl sulfide.

EXAMPLES 28 TO 52

The same procedure as in Example 27 was conducted with the exception of altering a combination of aromatic or heteroaromatic methyl sulfide used as the starting material and a halogenating agent to the compounds as shown below in Tables 4, 5 and 6, giving the corresponding aromatic or heteroaromatic sulfonyl halides.

TABLE 4

| Ex. | Starting Material | Halogenating agent | Product | Yield (%) |
|---|---|---|---|---|
| 28 | 2-Pyridyl methyl sulfide | Sulfuryl chloride | 2-Chlorosulfonylpyridine | 93.1 |
| 29 | 4-Pyridyl methyl sulfide | Sulfuryl chloride | 4-Chlorosulfonylpyridine | 94.5 |
| 30 | 2,6-Di(methylthio)pyridine | Sulfuryl chloride | 2,6-Di(chlorosulfonyl)-pyridine | 95.6 |
| 31 | 2-Pyrazyl methyl sulfide | Sulfuryl chloride | 2-Chlorosulfonylpyrazine | 94.3 |
| 32 | 4-Triazyl chloromethyl sulfide | Sulfuryl chloride | 4-Chlorosulfonyltriazine | 92.1 |
| 33 | 2-Oxazyl dichloromethyl sulfide | Sulfuryl chloride | 2-Chlorosulfonyloxazole | 92.8 |
| 34 | 4-Isothiazyl dichloromethyl sulfide | Sulfuryl chloride | 4-Chlorosulfonyl-isothiazole | 94.5 |
| 35 | 3,5-Dichlorophenyl dichloromethyl sulfide | Bromine | 3,5-Dichlorobenzenesulfonyl bromide | 90.2 |
| 36 | 4-Bromophenyl dichloromethyl sulfide | Bromine | 4-Bromobenzenesulfonyl bromide | 95.4 |
| 37 | 4-Bromophenyl trichloromethyl sulfide | Bromine | 4-Bromobenzenesulfonyl bromide | 92.1 |

TABLE 5

| Ex. | Starting Material | Halogenating agent | Product | Yield (%) |
|---|---|---|---|---|
| 38 | 1,4-Di(dichloromethylthio)benzene | Bromine | 1,4-Benzenedisulfonyl bromide | 90.2 |
| 39 | 1,4-Di(trichloromethyl-thio)benzene | Bromine | 1,4-Benzenedisulfonyl bromide | 94.1 |
| 40 | 1,2-Di(dichloromethylthio)- | Bromine | 1,2-Benzenedisulfonyl | 92.5 |

TABLE 5-continued

| Ex. | Starting Material | Halogenating agent | Product | Yield (%) |
|---|---|---|---|---|
| | benzene | | bromide | |
| 41 | 1,2-Di(dichloromethylthio)-4-butylbenzene | Bromine | 4-Butyl-1,2-benzene-disulfonyl bromide | 94.5 |
| 42 | 4-Cyanophenyl dichloromethyl sulfide | Bromine | 4-Cyanobenzenesulfonyl bromide | 93.0 |
| 43 | 2-Cyanophenyl dichloromethyl sulfide | Bromine | 2-Cyanobenzenesulfonyl bromide | 89.0 |
| 44 | 4-Nitrophenyl dichloromethyl sulfide | Bromine | 4-Nitrobenzenesulfonyl bromide | 91.2 |
| 45 | Methyl 4-(dichloromethylthio)-benzoate | Bromine | Methyl 4-(bromosulfonyl)-benzoate | 85.2 |
| 46 | 2-Cyano-3-chlorophenyl dichloromethyl sulfide | Bromine | 2-Cyano-3-chlorobenzene-sulfonyl bromide | 86.4 |

TABLE 6

| Ex. | Starting Material | Halogenating agent | Product | Yield (%) |
|---|---|---|---|---|
| 47 | 4,4'-Di(dichloromethylthio)-diphenyl sulfide | Bromine | 4,4'-Di(bromosulfonyl)-diphenyl sulfide | 82.3 |
| 48 | 4,4'-Di(dichloromethylthio)-2,2'-(dicyano)diphenyl sulfide | Bromine | 2,2'-(Dicyano)-4,4'-di(bromosulfonyl)diphenyl suifide | 82.6 |
| 49 | 4-(Phenylthio)phenyl dichloromethyl sulfide | Bromine | 4-(Phenylthio)phenyl-sulfonyl bromide | 95.0 |
| 50 | 4-(Phenylsulfonyl)phenyl dichloromethyl sulfide | Bromine | 4-(Phenylsulfonyl)phenyl-sulfonyl bromide | 85.0 |
| 51 | 1-Naphthyl dichloromethyl sulfide | Bromine | 1-Naphthylsulfonyl bromide | 95.0 |
| 52 | 2-Naphthyl dichloromethyl sulfide | Bromine | 2-Naphthylsulfonyl bromide | 90.1 |

What is claimed is:

1. A process for preparing an aromatic or heteroaromatic sulfonyl halide represented by the formula (3), the process comprising reacting an aromatic or heteroaromatic methyl sulfide represented by the formula (1) with a halogenating agent in the presence of water $$Ar\text{-}(SCH_{3-m}X_m)_n \quad (1)$$

$$Ar\text{-}(SO_2Y)_n \quad (3)$$

wherein Ar is an aromatic ring or a heteroaromatic ring which is unsubstituted or which has an optional substituent or substituents, X and Y are halogen atoms, m is an inter of 1 to 3 and n is 1 or 2.

2. The process according to claim 1, wherein X in the formula (1) is a chlorine atom.

3. The process according to claim 1, wherein m in the formula (1) is 1 or 2.

4. The process according to claim 1, wherein the halogenating agent is chlorine.

5. The process according to claim 1, wherein Ar in the formula (1) and the formula (3) is a benzene ring, pyridine ring, thiophene ring, thiazole ring or isothiazole ring, said rings being unsubstituted or having an optional substituent or substituents.

6. The process according to claim 1, wherein Ar in the formula (1) and the formula (3) is an aromatic ring or heteroaromatic ring having halogen, cyano group, nitro group, formyl group, alkylcarbonyl group, carboxyl ester group, carbamoyl group, alkyl group, alkoxyl group or substituted phenylthio group in an optional position or positions.

7. The process according to claim 1, wherein the compound represented by the formula (3) is 2-cyanobenzenesulfonyl chloride, 4-cyanobenzenesulfonyl chloride, 2-nitrobenzenesulfonyl chloride or 4-nitrobenzenesulfonyl chloride.

8. A process for preparing an aromatic or heteroaromatic sulfonyl halide represented by the formula (3), the process comprising reacting an aromatic or heteroaromatic methyl sulfoxide represented by the formula (2) with a halogenating agent in the presence of water $$Ar\text{-}(SOCH_{3-m}X_m)_n \quad (1)$$

$$Ar\text{-}(SO_2Y)_n \quad (3)$$

wherein Ar is an aromatic ring or a heteroaromatic ring which is unsubstituted or which has an optional substituent or substituents, X and Y are halogen atoms, m is an integer of 0 to 3 and n is 1 or 2.

9. The process according to claim 8, wherein X in the formula (2) is a chlorine atom.

10. The process according to claim 8, wherein m in the formula (2) is zero.

11. The process according to claim 8, wherein m in the formula (2) is 1 or 2.

12. The process according to claim 8, wherein the halogenating agent is chlorine.

13. The process according to claim 8, wherein Ar in the formula (2) and the formula (3) is a benzene ring, pyridine ring, thiophene ring, thiazole ring or isothiazole ring, said rings being unsubstituted or having an optional substituent or substituents.

14. The process according to claim 8, wherein Ar in the formula (2) and the formula (3) is an aromatic ring or heteroaromatic ring having halogen, cyano group, nitro group, formyl group, alkylcarbonyl group, carboxyl ester group, carbamoyl group, alkyl group, alkoxyl group or substituted phenylthio group in an optional position or positions.

15. The process according to claim 8, wherein the compound represented by the formula (3) is 2-cyanobenzenesulfonyl chloride, 4-cyanobenzenesulfonyl chloride, 2-nitrobenzenesulfonyl chloride or 4-nitrobenzenesulfonyl chloride.

\* \* \* \* \*

UNITED STATES PATENT AND TRADEMARK OFFICE
CERTIFICATE OF CORRECTION

PATENT NO. : 5,811,571
DATED : September 22, 1998
INVENTOR(S) : Hitoshi Karino, Hiroshi Goda, Jun-ichi Sakamoto, Katsuhiko Yoshida, Hideaki Nishiguchi It is certified that error appears in the above-identified patent and that said Letters Patent is hereby corrected as shown below:

On the title page: Please add Item [73] Assignee,

--Sumitomo Seika Chemicals Co., Ltd., Hyogo, Japan--.

Signed and Sealed this

Twenty-seventh Day of July, 1999

*Attest:*

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO.    : 5,811,571
DATED         : September 22, 1998
INVENTOR(S)   : Hitoshi Karino et al.

It is certified that error appears in the above-identified patent and that said Letters Patent is hereby corrected as shown below:

Column 9,
Line 47, delete "inter" and insert -- integer --.

Signed and Sealed this

Sixteenth Day of September, 2003

JAMES E. ROGAN
*Director of the United States Patent and Trademark Office*